United States Patent
Gust, Jr. et al.

(10) Patent No.: US 6,183,727 B1
(45) Date of Patent: Feb. 6, 2001

(54) USE OF LONG-WAVELENGTH ELECTROMAGNETIC RADIATION AND PHOTOPROTECTIVE TUMOR LOCALIZING AGENTS FOR DIAGNOSIS

(75) Inventors: John Devens Gust, Jr., Tempe; Ana L. Moore; Thomas A. Moore, both of Scottsdale, all of AZ (US); William H. Ralston, St. Charles, MO (US)

(73) Assignee: Arizona Board of Regents, Tempe, AZ (US)

( * ) Notice: Under 35 U.S.C. 154(b), the term of this patent shall be extended for 0 days.

(21) Appl. No.: 09/282,610

(22) Filed: Apr. 1, 1999

Related U.S. Application Data

(63) Continuation of application No. 09/081,175, filed on May 19, 1998, now abandoned.

(51) Int. Cl.$^7$ .............................. A61B 10/00; A61K 49/00
(52) U.S. Cl. ............................ 424/9.61; 424/9.6; 424/9.1
(58) Field of Search .................................. 424/9.61, 9.6, 424/9.1; 600/317; 436/172, 800; 540/139, 140, 145; 514/185, 410

(56) References Cited

U.S. PATENT DOCUMENTS

| 5,286,474 | 2/1994 | Gust, Jr. et al. | 424/7.1 |
|---|---|---|---|
| 5,534,506 | * 7/1996 | Morgan et al. | 514/185 |
| 5,552,134 | 9/1996 | Morgan et al. | 424/9.61 |
| 5,610,175 | 3/1997 | Vogel et al. | 514/410 |
| 5,637,608 | 6/1997 | Vogel et al. | 514/422 |

FOREIGN PATENT DOCUMENTS

| WO9408631 | 4/1994 | (WO) . |
|---|---|---|
| WO9746262 | 12/1997 | (WO) . |

OTHER PUBLICATIONS

Gust et al. (1993) Ann. New York Acad. Sci. 691:32.
Mathews–Roth (1984) Photochem. Photobiol. 40:63.
Nilsson et al. (1997) Br. J. Cancer 76:355.
Osuka et al. (1990) Chem. Lett. 10:1905.
Saarnak et al. (1998) Lasers Med. Sci. 13:22.
Tatman et al. (1998) Photochem. Photobiol. 68:459.
Cardoso et al. (1996) J. Braz. Chem. Soc. 7:19.
Gust et al. "Methods in Enzymology", vol. 213, Carotenoids Part A, Chemistry, Separation, Quantitation, and Antioxidation, Edited by Lester Packer (1992), pp. 87–101.
Bensasson et al., "Mimicry of Antenna and Photoprotective Carotenoid Functions by a Synthetic Carotenoporphyrin", Nature, vol. 290, No. 5804, pp. 329–332 (Mar. 26, 1981).
Dirks et al., "Light Absorption and Energy Transfer in Polyene–Porphyrin Esters", Photochemistry and Photobiology, vol 32, pp. 277–280 (1980).
Frank et al., "Triplet–Triplet Energy Transfer in B800–850 Light–Harvesting Complexes of Photosynthetic Bacteria and Synthetic Carotenoporphyrin Molecules Investigated by Electron Spin Resonance", Biochimica et Biophysica Acta 892 (1987) pp. 253–263.
Kuciauskas et al., "Structural Effects on Photoinduced Electron Transfer in Carotenoid—Porphyrin—Quinone Triads", J. Phys. Chem. B (1997), vol. 101, No. 3, pp. 429–440.
Osuka et al., "An Improved Synthesis of 5,15–Diaryloctaalkylporphyrins", J. Heterocyclic Chem., vol. 27, pp. 1657–1659 (1990).
Gunter et al., "Purpurins Bearing Functionality at the 6,16–meso–Positions: Synthesis from 5,15–Disubstituted meso–[β–(Methoxycarbonyl)vinyl]porphyrins", Aust. J. Chem., vol. 43, pp. 1839–1860 (1990).

* cited by examiner

Primary Examiner—Michael G. Hartley
(74) Attorney, Agent, or Firm—Baker Botts

(57) ABSTRACT

A process of pathology or target tissue identification comprising administering an imaging material to a pathology or target tissue bearing mammalian host and irradiating the mammalian host with electromagnetic radiation having a wavelength between about 600 and 1100 nm, and especially in the region of 700 nm and longer wavelengths, whereupon the imaging material, which has been preferentially taken up by the pathology or target tissue, emits light and permits precise identification of the location, size and/or shape of the pathology or target tissue.

8 Claims, No Drawings

USE OF LONG-WAVELENGTH ELECTROMAGNETIC RADIATION AND PHOTOPROTECTIVE TUMOR LOCALIZING AGENTS FOR DIAGNOSIS This is a continuation of application Ser. No. 09/081,175 filed May 19, 1998, now abandoned.

BACKGROUND OF THE INVENTION

This invention relates to a method of diagnosing mammalian pathology or target tissues and more particularly to a photoidentification method of diagnosing pathology or target tissue using an optical imaging material containing an imaging agent and at least one auxiliary chromophore. The imaging material preferentially localizes in pathology or target tissue, absorbs light and in some cases fluoresces or phosphoresces upon exposure to light. The primary purpose of the auxiliary chromophore is prevention of photodamage to healthy tissue by the agent.

Certain classes of molecules, including, for example, synthetic porphyrin derivatives, naturally occurring porphyrins and their derivatives, chlorophylls and their derivatives, purpurins, phthalocyanines, other cyclic tetrapyrroles, and fullerenes can act as imaging, detection and diagnostic agents for pathologies or target tissues including tumors, atherosclerotic and arthritic tissue, and diseased blood vessels. Administration of these agents to a human or other organism results in preferential localization of the agent in any of a variety of pathologies with respect to surrounding tissue. Irradiation of the organism with light of a given wavelength or wavelengths results in absorption of light by the agent. In some cases, the agent then emits light by fluorescence or phosphorescence. Light absorption or light emission produces contrast between the pathology or target tissue and the surrounding tissue, and the detection of this contrast allows pathology or target tissue imaging, detection or diagnosis. Alternatively, agents of this type can be used to enhance contrast or otherwise improve detection in magnetic resonance imaging of pathology or target tissues or can bear radioactive isotopes whose detection can be the basis of pathology or target tissue imaging, detection and diagnosis, or can serve as contrast agents for X-ray radiological or other techniques involving high-energy radiation.

Absorption of light by the agent results in production of excited states. These excited states are by definition of higher energy than the original unexcited ground state of the agent. The excess energy can result in deleterious interactions with the organism. For example, excited triplet states of the agent (or singlet or other excited states) can react directly with tissue or other components of the organism to cause damage to the organism. Triplet states and other states of high multiplicity can also cause the formation of excited states of oxygen, such as singlet oxygen, and other powerful oxidizing agents, superoxides, and other oxygen radicals. These excited states of oxygen and oxygen radicals are known to cause damage to biological membranes as well as other components of the organism. The agent in an excited state can also react with other molecules present to create other species that are harmful to the organism. Such damage is not limited to pathology or target tissue, as the agent does not localize exclusively in the pathology or target tissue. After administration some agent is found throughout the organism, including the skin. This propensity to cause damage to healthy tissue in the organism can limit the usefulness of the agent for pathology or target tissue imaging detection and diagnosis.

Carotenoid pigments, which are ubiquitous in photosynthetic membranes, are essential for the survival of green plants. Three facets of carotenoid function are recognized in photosynthetic membranes. First, carotenoids photoprotect by rapidly quenching chlorophyll triplet states which are formed in antenna systems or photosynthetic reaction centers. This triplet-triplet energy transfer prevents chlorophyll-photosensitized formation of highly destructive singlet oxygen which is injurious to the organism. In addition, carotenoids act as antennas by absorbing light in spectral regions where chlorophyll absorbs weakly and by delivering the resulting excitation to chlorophyll via a singlet-singlet energy transfer process. Finally, nearby carotenoids quench chlorophyll first excited singlet states. This quenching has been ascribed to energy transfer or electron transfer or some other process leading to internal conversion and is believed to play a role in the regulation of photosynthesis.

A number of porphyrin materials have been found to localize in pathologies and damage that tissue upon irradiation with light. Many of these, such as "hematoporphyrin derivative" and related materials, are being investigated as photodynamic therapeutic agents. All of these agents suffer from the problem that they are also absorbed by healthy tissue, which is consequently harmed by light.

Various synthetic carotenoids designed to mimic carotenoid photo protection have been investigated. Synthetic carotenoporphyrins consisting of a carotenoid part covalently linked to a synthetic meso-tetraarylporphyrin which successfully exhibited the photophysical functions of cartenoids in photosynthesis were first reported by G. Dirks, A. Moore, T. Moore and D. Gust in *Photochemistry and Photobiology,* Vol. 32, pp. 277–280 (Permagon Press Ltd. Great Britain, 1980).

A carotenoporphyrin which demonstrated quenching of the porphyrin triplet state by the attached carotenoid via triplet-triplet energy transfer was reported by R. V. Bensasson, E. J. Land, A. L. Moore, R L. Crouch, G. Dirks, T. A. Moore and D. Gust in *Nature,* Vol. 290, No. 5804, pp. 329–332 (Mar. 16, 1981). Since that time, various compounds which exhibit such triplet-triplet energy transfer have been reported. In 1984, five carotenoporphyrins were prepared by Dr. Paul Liddell at Arizona State University and reported in his doctoral thesis dated December 1985. Three carotenoporphyrins were reported by H. Frank, B. Chadwick, J. Oh, and D. Gust et al. in *Biochemical et Biophysical Acta* 892 (1987), pp. 253–263.

It has also been previously shown in U.S. Pat. No. 5,286,474, incorporated by reference herein, that certain synthetic carotenoporphyrins preferentially localize in mammalian pathology or target tissue where they absorb and emit light when irradiated with light so that the site of the pathology or target tissue may be detected by the fluorescence of the localized carotenoporphyrin.

SUMMARY OF THE INVENTION

This invention comprises the use of at least one auxiliary chromophore, such as carotenoids and other polyenes, to prevent undesired damage to tissue that can be caused by agents, as described above. The auxiliary chromophore is placed in the vicinity of the agent, through chemical bonding or other means, in such a way that it rapidly removes the excitation energy of the agent before that energy can cause substantial damage to the organism or sensitize the formation of singlet oxygen or other harmful species. The energy is removed through triplet-triplet energy transfer, single-singlet energy transfer, or other quenching phenomena. The energy thus acquired by the auxiliary chromophore is in a form that is essentially harmless to the organism, and is rapidly dissipated in a harmless way.

Localization of the imaging material employed in the practice of this invention is advantageous over the use of porphyrins alone. In addition, photodamage of tissue is advantageously precluded by the quenching of the porphyrin triplet state, and most importantly, photopenetration of the tissue by excitation light and by emitted light is enhanced by the use of agents that absorb and emit lower energy (longer wavelength) electromagnetic radiation. Thus this invention overcomes the problem of collateral tissue damage inherent with the use of existing photosensitizing compounds as diagnostic agents, and increases the detection of pathology or target tissues by using longer wavelength electromagnetic radiation.

This invention also provides a method of locating and visualizing mammalian pathology or target tissue. The method comprises administering a diagnostically effective amount of an imaging material, comprising an agent and at least one auxiliary chromophore, to a mammalian host, permitting the diagnostic agent to localize in the pathology or target tissue and thereafter irradiating the mammalian host with low energy electromagnetic radiation having a wavelength between about 600 and 1100 nm. The localized imaging material thus absorbs and in some cases fluoresces, or otherwise luminesces sharply defining the pathology or target tissue. Light absorbed by or emitted from the pathology or target tissue by the localized diagnostic agent employed in this invention sharply defines the location of the pathology or target tissue to be removed or otherwise treated. At the same time, the auxiliary chromophore prevents or limits photodamage to healthy tissue by quenching excited triplet states of the agent. In the event that the imaging process involves a process other than absorption or emission of light, the auxiliary chromophore still provides protection from photodamage by adventitious light in any tissues.

Generally, the imaging materials of the present invention may be effectively administered to representative mammals in dosages of from 0.5 to 50 $\mu$mol/kg of host body weight, preferably from 3 to 48 hours prior to the diagnostic procedure or surgery.

The imaging materials employed in this invention have a number of advantages over current contrast agents and pathology or target tissue diagnostic procedures. They lack toxicity due to the antioxidant behavior of the auxiliary chromophore and the use of lower energy, higher wavelength electromagnetic radiation. Many individuals are sensitive to present X-ray contrast agents employed, for example in computer assisted tomography (CAT) scans, and there have been cases of severe allergy reactions resulting in anaphylactic shock. In addition, the patient is exposed to ionizing radiation. Alternatively, nuclear scans are often employed. However, nuclear scans require the administration of radioactive diagnostic materials and further, are useful primarily to define function as opposed to structure. Magnetic resonance imaging is accurate and definitive for the diagnosis of brain and other abnormalities but is expensive, unpleasantly noisy, confining for claustrophobic individuals, and often times the contrast agent enhancement is not target specific. This invention is advantageous over these alternative techniques. Lower cost is an additional advantage of this invention.

The present invention also provides an improved, more convenient and economical synthesis of the diagnostic agents employed herein.

DETAILED DESCRIPTION OF THE INVENTION

An imaging material comprising at least two parts is employed in this invention. One part is an agent which localizes in pathology or target tissue in preference to surrounding tissue, absorbs light to produce an excited state, and allows imaging, demarcation, detection or diagnosis of the pathology or target tissue, or combinations thereof, via the absorption of light, or the emission of fluorescence, phosphorescence or heat. These effects can be detected via absorption spectroscopy, fluorescence or phosphorescence spectroscopy, or heat detection by calorimetric methods such as photothermal, photoacoustic, or mirage effect. Alternatively, the agent can enhance imaging as a magnetic resonance imaging contrast agent or by bearing radioactive isotopes of any of various elements whose radioactive emissions can be detected and used for imaging and diagnostic purposes, or by acting as a contrast agent for imaging by X-radiation or other high-energy radiation. The second part comprises an auxiliary chromophore, such as a carotenoid, polyene, or other chromophore with a low-energy triplet, singlet or charge-separated state, which is held in the vicinity of the agent through chemical bonding or other mechanisms, and which prevents damage to the organism by quenching high-energy states of the agent via triplet-triplet energy transfer, singlet-singlet energy transfer, electron transfer, or similar mechanisms.

Examples of preferred imaging materials include

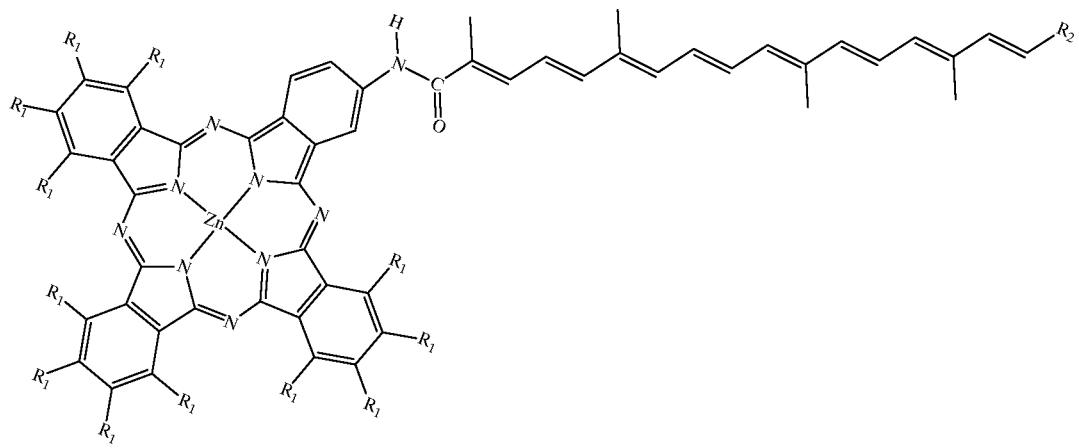

wherein
R$_1$=hydrogen, alkyl or alkoxy groups; optionally the alkyl or alkoxy groups may include other groups such as COOH groups and the like,
R$_2$=alkyl or aryl groups; the alkyl or aryl groups may include other groups such as COOH groups, NH$_2$ groups and the like;

wherein
R$_1$=hydrogen, alkyl or alkoxy groups; the alkyl or alkoxy groups may include other groups such as COOH groups, NH$_2$ groups and the like,
R$_2$=hydrogen, alkyl or aryl groups; the alkyl or aryl groups may include other groups such as COOH groups, NH$_2$ groups and the like;

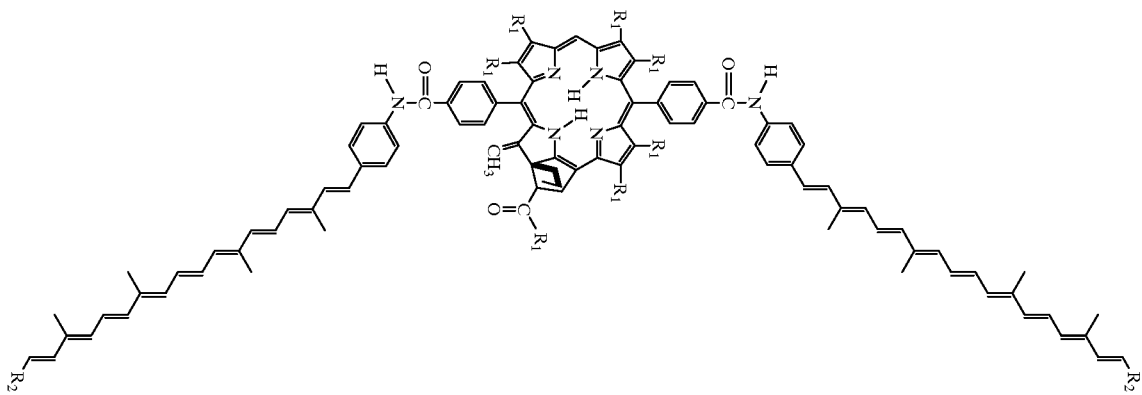

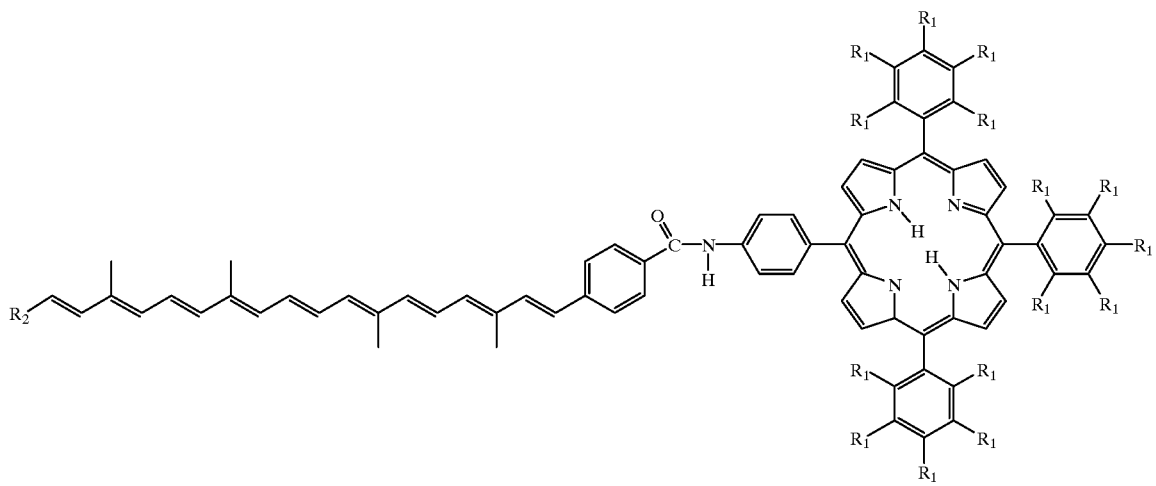

wherein
R$_1$=hydrogen, alkyl or alkoxy groups, wherein at least one R$_1$ is an alkoxy group; the alkyl or alkoxy groups may include other groups such as COOH groups and the like,
R$_2$=hydrogen, alkyl or aryl groups; the alkyl or aryl groups may include other groups such as COOH groups, NH$_2$ groups and the like; and

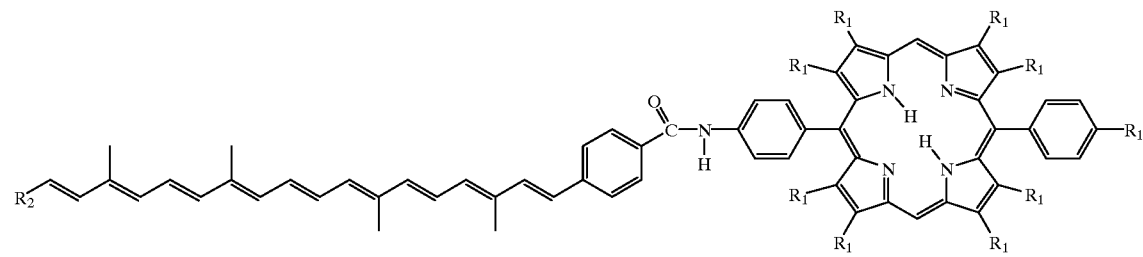

wherein
R$_1$=alkyl, alkoxy or aryl groups, the alkyl, alkoxy and aryl groups may include COOH groups and the like,
R$_2$=alkyl or aryl groups, the alkyl and aryl groups may include COOH groups, NH$_2$ groups and the like.

Administration of the imaging material to a human or other organism via methods including ingestion, injection (either alone or with a carrier such as an emulsifier, liposomes, or other biocompatible materials), inhalation or direct topical or internal application is followed by movement of the imaging material through the tissues of the organism, and concentration of the imaging material in pathological tissue, relative to surrounding tissue. The pathology or target tissue may be optically imaged, delineated, detected or diagnosed by: (i) illuminating the area containing the preferentially localized imaging material with light at any wavelength absorbed by the imaging material; and (ii) the absorption or the emission of light through fluorescence or phosphorescence or the generation of heat by this material. Detection of absorption or emission of light can be by the human eye, photomultiplier, photosensitive diode, or by any suitable device for detection of light at the appropriate wavelengths. Heat can be detected by photothermal, photoacoustic, mirage effect, or other calorimetric methods. Alternatively, if the agent is a magnetic resonance contrast agent, detection is by magnetic resonance imaging instrumentation. If the agent contains a radioactive isotope, radiation from this isotope can be detected. If the agent is an X-ray contrast material, pathology or target tissue can be imaged and identified using X-ray radiological techniques.

The optical agent, after excitation with light, will form excited singlet states, and may form excited triplet states or other high-energy states. In general, such states can react chemically with the organism, causing tissue damage, or react with oxygen to form harmful singlet oxygen or radical species, or with other molecules that may be present to produce other reactive, high energy species than may in turn react with the organism, causing tissue damage. In the imaging material, the auxiliary chromophore quenches the excited state or other high-energy state of the agent via an energy or electron transfer process. This quenching process produces a low-energy state, such as the polyene triplet state, or singlet state, which is incapable of harming the organism, and is incapable of sensitizing the formation of singlet oxygen or other reactive species. The method of coupling the auxiliary chromophore to the agent and the proper choice of agent and auxiliary chromophore ensure that this quenching is a rapid process. The method of coupling the auxiliary chromophore to the agent is facilitated through the overlap of electronic orbitals which may occur by either chemical bonding, Van der Waals interaction, or by using a coupling compound such as a protein to hold the auxiliary chromophore and the agent in near proximity. This rapid quenching deactivates the high energy triplet or other state of the agent before it can interact deleteriously with tissue, sensitize singlet oxygen formation, or react with other molecules that may be present to form a harmful species. In essence, the auxiliary chromophore allows the agent to perform as an imaging or detection agent, but prevents it from significantly damaging the organism.

In this invention, a method of administering an imaging material that will preferentially localize in pathology or target tissue and absorb and emit light without damaging the mammalian host upon irradiation with light comprises the steps of administering a diagnostically effective amount of the imaging materials and allowing said imaging material to circulate and accumulate and localize in pathology or target tissue, preferably from about 3 to 48 hours prior to the diagnostic or surgical procedure, and exposing the mammalian host to light causing the imaging material to absorb and fluoresce and thereby permitting visualization and definition of the pathology or target tissue to be removed or treated, or using some other visualization method such as those described hereinabove.

More specifically, the imaging material employed in the practice of this invention localizes in pathology or target tissue, absorbs light of one wavelength, may emit light of another wavelength, but does not damage healthy tissue. The process of this invention may be used both for diagnosis and as a valuable adjunct to surgery as light emitted from the pathology or target tissue by the localized agent in the imaging material would sharply define the location of the pathology or target tissue to be removed.

In practice, an imaging material is administered intravenously to a mammalian host in a dosage of from 0.5 to 50 μmol/kg of body weight from 1 to 72 hours prior to exposure to radiation having a wavelength of from about 600 to about 1,100 nanometers. The imaging materials may be conveniently administered either solubilized in a biocompatible emulsion such as a Tween-80, CREMOPHOR EL emulsion (Sigma Chemical Company) or other suitable lipophilic emulsion or incorporated into liposomes such as unilamellar or multilamellar liposomes of a synthetic lipid such as dipalmitoylphosphatidylcholine (DPPC) sold by Sigma Chemical Company, Inc. After the photosensitive imaging material has had sufficient time to circulate and localize in pathology or target tissue, the mammalian host is exposed to a light so that the imaging material localized in pathology or target tissue absorbs and fluoresces permitting visualization of the pathology or target tissue location, size and configuration. The most suitable electromagnetic radiation sources, e.g. light sources, are those that emit radiation at wavelengths of between 600 to about 1,100 nanometers. The imaging agents of this invention have their red-most absorption bands in the range of about 600 to 1,100 nanometers.

The use of imaging materials that absorb electromagnetic radiation in the 600–1,100 nm region permits the diagnostic light to penetrate the tissue more deeply and image deeper pathology or target tissue tissues than can be obtained with molecules that absorb only at shorter wavelengths. Thus, monochromatic radiation at these wavelengths would be preferentially absorbed. In addition to using the human eye as a detector, a light-sensitive electronic device such as a photomultiplier or photodiode array could be used as a detector to provide a picture or electronic image of localized material. Alternatively, any other detection and visualization method for the agent may be employed. Even if light is not part of the diagnostic process, the auxiliary chromophore will protect the skin and other tissues of the organism from photodamage by adventitious light absorbed by the agent.

EXAMPLES

To further assist in the understanding of the present invention and not by way of limitation, the following examples are presented. In the examples reported below, the $^1$H NMR spectra were obtained at 300 to 500 MHZ and used $\leq 1\%$ solutions in chloroform-d with tetramethylsilane as an internal reference. The UV-vis spectra were recorded on a Hewlett Packard 8450A spectrophotometer. For transient absorption studies, samples were placed in 1 cm×1 cm×4 cm cuvettes and deoxygenated by bubbling with argon. The apparatus used for the transient absorption work features excitation with ca. 5 ns pulses of less than approximately 5 mJ at 590–700 nm. An adequate signal-to-noise ratio was achieved by signal averaging (typically about 500 flashes). The details of the spectrometer are described by Gust et al. *J Am. Chem. Soc.* 1986, 108, 8028, incorporated by reference herein. Fluorescence decay measurements were made on ca. $1\times10^{-5}$M solutions using the time-correlated single photon counting method. The excitation source was a frequency-doubled, mode-locked Nd—YAG laser coupled to a synchronously pumped, cavity dumped dye laser with excitation at 590 nm. Detection was via a microchannel plate photomultiplier (Hamamatsu R2809U-01), and the instrument response time was ca. 35 ps.

Example 1

(Carotenophthalocyanines with short carotenoids)

Carotenophthalocyanines consisting of a nine-double bond carotenoid polyene (the auxiliary chromophore). covalently linked to a synthetic zinc-phthalocyanine (the agent)

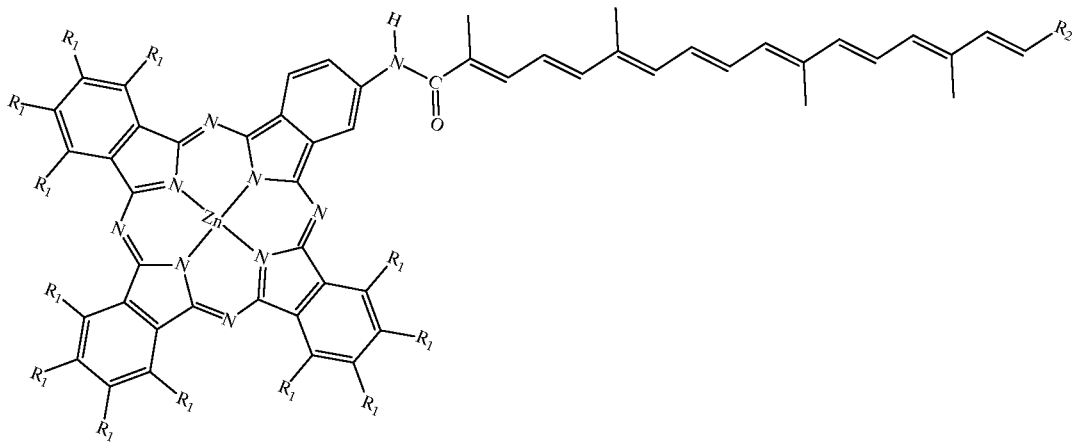

wherein

R₁=hydrogen, substituted or unsubstituted alkyl or alkoxy group,

R₂=hydrogen, substituted or unsubstituted alkyl or aryl group, as exemplified by the chemical compound

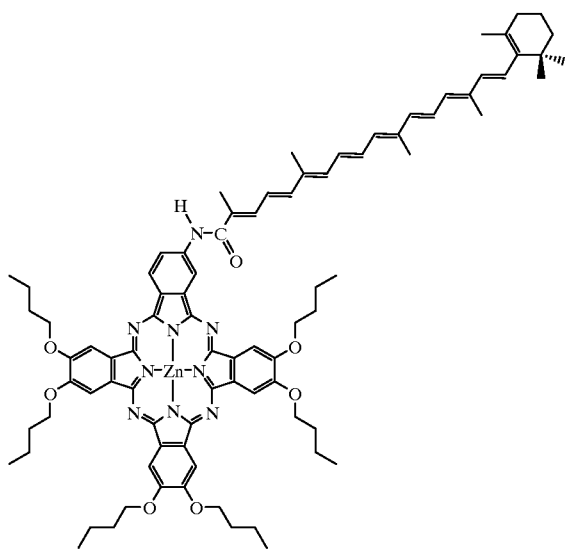

have been synthesized as follows:

A portion of 4-nitrophthalonitrile (5.15 g, 29.8 mmole) was dissolved in 125 mL methanol in a hydrogenation flask. The catalyst, 10% Pd/C (515 mg), was added to the mixture which was then flushed with $H_2$ and stirred under 50 psi of $H_2$ for 1 hour. The catalyst was removed by filtration and the solvent was distilled off under vacuum. The desired 4-aminophthalonitrile was obtained in 86% yield (3.66 g).

4-Aminophthalonitrile (3.60 g, 25.2 mmole) was dissolved in 8.6 mL of pyridine. Hexanoyl chloride (8.6 mL, 61.5 mmole) was added and the mixture was stirred under $N_2$ for 2 hours. The pyridine was distilled under vacuum until a yellow-orange residue was obtained. This residue was dissolved in dichloromethane and washed with 0.1 M HCl (5×15 mL) and then neutralized with aqueous sodium bicarbonate (3×50 mL). The organic solution was separated and dried over magnesium sulfate. Purification by column chromatography (silica, dichloromethane: methanol 5%) afforded 4.3 g (71% yield) of 4-hexanamidophthalonitrile as a light yellow compound.

Catechol (13.21 g, 120.1 mmole) was dissolved in 120 mL of dimethylformamide (DMF). Potassium carbonate (41.42g) and butyl bromide (49.22 g) were added to the solution. The mixture was stirred under $N_2$ for 24 hours at 95° C. Excess potassium carbonate and butyl bromide (30 g of each) were added and the mixture was stirred overnight. Another addition of 30 g of butyl bromide and further stirring overnight was necessary to complete the reaction. The mixture was diluted with 1 L of ether and washed with water (6×250 mL) and then dried over magnesium sulfate. The ether was removed by distillation under vacuum, yielding a viscous brownish liquid. The liquid product was purified by distillation under vacuum. The fractions with a boiling point between 69–73° C. were collected. A yellow liquid identified as 1,2-dibutoxybenzene (19.05 g, 71.5% yield) was obtained.

A portion of 1,2-dibutoxybenzene (19.0 g, 85.6 mmole) was dissolved in 175 mL of dichloromethane. The solution was cooled to 0° C. and kept under $N_2$ while $Br_2$ (9.6 mL 186.8 mmole) dissolved in 25 mL dichloromethane was added slowly. Half of the $Br_2$ solution was added while the temperature was kept at 0° C. and the other half was added after the temperature was raised to 25° C. The reaction mixture was stirred for 2 hours under $N_2$. The work-up consisted of a wash with aqueous sodium hydrogen sulfate until the yellow color disappeared, followed by two washes with sodium bicarbonate solution. The organic solution was dried over sodium sulfate and filtered. Evaporation of the solvent afforded 31.71 g of 1,2-dibromo-4,5-dibutoxybenzene as a clear liquid (97.5% yield).

A portion of 1,2-dibromo4,5-dibutoxybenzene (31.7 g, 83.5 mmole) was dissolved in DMF, 22.8 g (254.6 mmole) of cuprous cyanide was added and the suspension was stirred and heated to reflux under $N_2$ for 6 hours. The mixture was cooled to room temperature and poured into 1.1 L of ammonium hydroxide (30%), whereupon a blue liquid with a green froth formed. Air was bubbled through the liquid for 20 hours. The solid was removed by filtration, washed with 10% ammonium hydroxide until the filtrate was clear, and then washed with water to neutral pH. The green powder was extracted with hexanes in a Soxhlet extractor for one week. The solvent volume was reduced to 200 mL, whereupon a solid formed. The powder was collected and recrystallized giving 10.53 g (46% yield) of white crystals of 4,5-dibutoxyphthalonitrile.

4-Hexanamidophthalonitrile (1.467 g, 6.1 mmole) and 4,5-dibutoxyphthalonitrile (2.48 g, 9.1 mole) were dissolved in 80 mL of 2-dimethylaminoethanol and stirred under an ammonia flow at 100° C. for 2 hours 1.8-diazabicyclo[5.40]undecene-7 (DBU) (1.3 mL) was added and the stirring was continued for 15 minutes. Zinc acetate (1.146 g) was added and the mixture was stirred at 100° C. overnight. The green mixture was cooled to room temperature and 60 mL water:methanol (1:1) was added. The precipitate formed was collected, washed with water and dried. The product was purified by column chromatography (silica, chloroform:methanol 1%). Zinc 9,10,16,17,23,24-hexabutoxy-2-hexanamidophthalocyanine, was obtained in 18.5% yield (790 mg). $^1$H-NMR (500 MHZ, DMSO-CDCl$_3$) δ 1.02 (3H, t, —CO(CH$_2$)$_4$CH$_3$), 1.12 –1.20 (18H, m, —OCHCH$_2$CH$_2$CH$_3$), 1.47–1.53 (4H, m, —CO(CH$_2$)$_2$CH$_2$CH$_2$CH$_3$), 1.70–1.80 (12H, m,—OCH$_2$CH$_2$CH$_2$CH$_3$), 1.87 (2H, q, —COCH$_2$CH$_2$(CH$_2$)$_2$CH$_3$), 2.00–2.10 (12H, m, — OCH$_2$CH$_2$CH$_2$CH$_3$), 2.63 (2H, t, —COCH$_2$(CH$_2$)$_3$CH$_3$), 4.47–4.55 (12H, m, —O—CH$_2$CH$_2$CH$_2$CH$_3$), 8.40 (1H, d, J=8 Hz, Pc 3-H), 8.45–8.60 (6H, m, Pc 8,11,15,18,22,25-H), 9.10 (1H, d, J=8 Hz, Pc 4-H), 9.60 (1H, d, Pc 1-H), 10.6(1 H, s, —NHCO—); MS m/z: 1437.3 (M+2)$^+$; UV/vis (95% CH$_2$Cl$_2$–5% CH$_3$OH) 352, 454, 616, and 683 nm.

The phthalocyanine obtained in the reaction above (290 mg, 0.26 mmole) was dissolved in 40 mL of tetrahydrofuran (THF) and 40 mL of a saturated methanolic solution of KOH. The solution was heated to 75° C. and stirred overnight under N$_2$. An extra amount of THF (10 mL) was added and the mixture was stirred overnight. The reaction mixture was diluted with chloroform, the solution was washed with water (3×), the organic layer was dried over sodium sulfate and filtered, and the solvent was distilled. The desired zinc 2-amino-9,10,16,17,23,24-hexabutoxyphthalocyanine (214 mg) was obtained in 81% yield.

A portion of ethyl-β-apo-8'-carotenoate (62 mg, 0.13 mmole) prepared in accordance with O. Isler et al., Helv. Chim. Acta, 1959, 42, 864, was dissolved in 14 mL of THF. A solution of 1.2 g of KOH in 10 mL of methanol was added and the mixture was stirred under N$_2$ overnight. THF (2 mL) was added and the stirring was continued overnight. The reaction mixture was diluted with chloroform and neutralized with 20% acetic acid and washed with water. The solvent was distilled under vacuum. β-apo-8'-carotenoic acid (49 mg) was obtained in 84% yield.

The carotenoic acid prepared above (49 mg, 0.11 mmole) was dissolved in 6 mL of toluene and 2 mL of pyridine. One drop of thionyl chloride was added and the mixture stirred under N$_2$ for 15 minutes. The solvent was distilled under vacuum and the residue was kept under vacuum for an extra 15 minutes. The residue was redissolved in 2.5 mL of pyridine and 6 mL of dry chloroform. The aminophthalocyanine prepared above (100 mg, 0.098 mmole) dissolved in 6 mL chloroform was added to the solution of the acid chloride and the mixture was stirred overnight under N$_2$. The reaction mixture was diluted with chloroform, washed with water and dried under vacuum. The product was purified by column chromatography (silica, chloroform-methanol 0.2%). A second column (silica, chloroform) was necessary to obtained 73 mg (52% yield) of pure material shown in FIG. 1. $^1$H-NMR (500 MHZ, DMSO-CDCl$_2$) δ 1.01–1.04 (6H, m, Car 16-CH$_3$, Car 17-CH$_3$), 1.16–1.21 (18H, m, —OCH$_2$CH$_2$CH$_2$CH$_3$), 1.46 (2H, m, Car 2-CH$_2$), 1.59 (2H, m, Car 3-CH$_2$), 1.71 (3H, s, Car 18-CH$_3$),1.75–1.83 (12H, m, —OCH$_2$CH$_2$CH$_2$CH$_3$),1.96 (3H, s, Car 19-CH$_3$), 2.00 (3H, s, Car 20-CH$_3$), 2.08 (15H, m, —OCH$_2$CH$_2$CH$_2$CH$_3$, Car 20'-CH$_3$), 2.32 (3H, s, Car 19'-CH$_3$), 4.50–4.57 (12H, m, —O—CH$_2$CH$_2$CH$_2$CH$_3$), 6.16–6.8.1 (1H, m, Car=CH—), 7.44 (1H, d, J=10 Hz, Car 10'-H), 8.45–8.6 (7H, m, Pc 4,8,11,15,18,22,25-H), 9.1 (1H, d, J=8 Hz, Pc 3-H), 9.63 (1H, s, Pc 1-H), 10.4 (1H, s, —NHCO—); MS m/z: 1437.3 (M+2)$^+$; UV/vis (95% CH$_2$Cl$_2$ - 5% CH$_3$OH) 352, 454, 616, and 683 nm.

These carotenophthalocyanines are designed to be administered by injection or other means, to localize preferentially in pathology or target tissue tissue, and to absorb light, especially in the 700 nm region, and thereupon fluoresce at a longer wavelength than the absorbance wavelength in accordance with the general description above. The use of diagnostic light having a wavelength in the 700 nm region allows for deeper penetration of the light, for imaging deeper pathology or target tissue tissues, and for reducing tissue damage relative to light at shorter wavelengths. Light absorption, fluorescence, or both can be detected by either eye or instrumental methods, thus identifying and demarcating the pathology or target tissue tissue.

This class of carotenophthalocyanines bears relatively short, 9 double bonds or fewer, carotenoid moieties, which serve to enhance the fluorescence yield relative to related molecules with longer carotenoid polyenes. Furthermore, these compounds are designed to quench the phthalocyanine triplet states by triplet-triplet energy transfer to the attached carotenoid. This will prevent formation of singlet oxygen by energy transfer from the porphyrin triplet states, and thus prevent damage to healthy tissue caused by singlet oxygen, or long-lived porphyrin triplet states. These molecules are also designed to be readily excreted by normal tissue, including the liver and spleen.

Example 2

(Type B carotenopurins)

Molecules consisting of one or more carotenoid polyenes (the auxiliary chromophore) covalently linked to a type B purpurin (the agent) such as

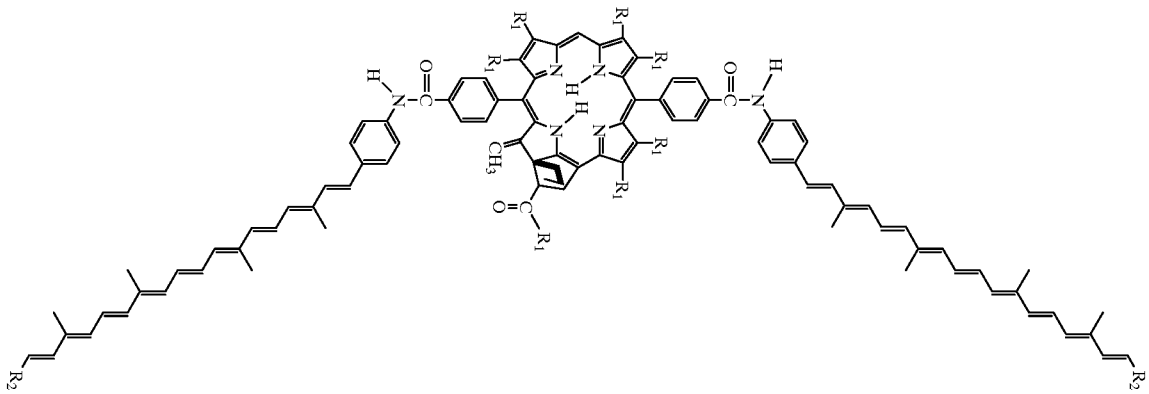

wherein
R₁=hydrogen, substituted or unsubstituted alkyl or alkoxy groups; each R₁ may be the same or different,
R₂=hydrogen, substituted or unsubstituted alkyl or aryl groups, each R₂ may be the same or different,
as exemplified by
have been synthesized as follows:

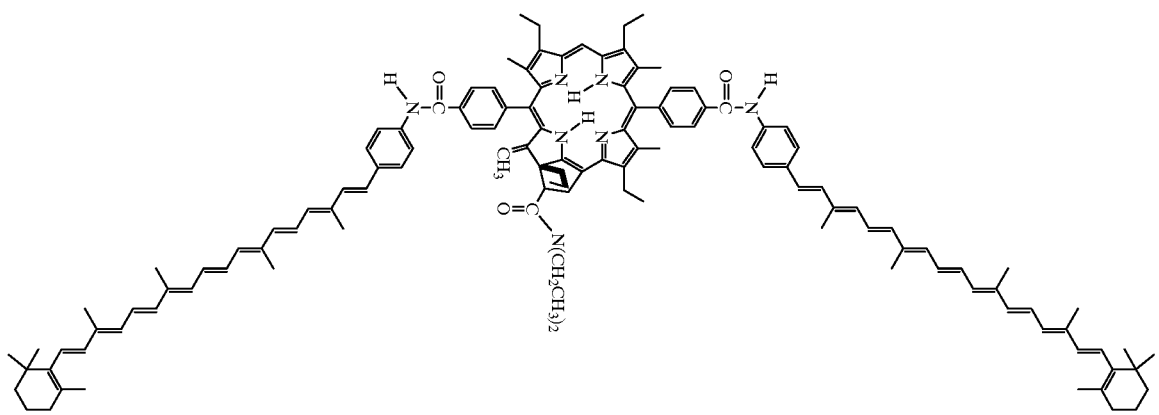

The starting porphyrin: 5,15-bis-(4-carbomethoxyphenyl)-2,8,12,8-tetraethyl-3,7,13,17-tetramethylporphyrin was prepared according to A. Osuka T. Nagata, F. Kobayashi and K. Maruyama, Heterocyclic Chem., 1990, 21, 1657–1659. The pure compound was obtained in 17% yield. ¹H-NM (300 MHZ, CDCl₃) δ −2.21 (2H, brs, —NH), 1.77 (12H, t, —CH₂CH₃) 2.47 (12H, s, —CH₃), 4.02 (8 H, q, —CH₂CH₃), 4.14 (6H, s, —CO₂CH₃), 8.12 (4H, d, Ar—H), 8.45 (4H, d, Ar—H), 10.26 (2H, s, H meso); MS m/z: 747.3 (M+H)⁺ (Calc. M=746.4); UV/vis (CH₂Cl₂) 235, 408, 508, 542, 576, 628 nm.

To a 1L round bottomed flask equipped with a stirring bar was added 1.0 g (1.34 mmole) of the porphyrin prepared above and 400 mL of toluene. To the suspension was added 3.0 g (11 mmole) of nickel acetoacetate (Ni(AcAc)₂,H₂O) and the temperature was raised to 100° C. for 48 hours. After this period all the free base porphyrin was converted to the nickel analog. The solvent was partially removed and the pasty solid was redissolved in chloroform. The solution was washed with water, dried over anhydrous sodium sulfate and filtered, and the solvent was evaporated. The residue was recrystallized from CHCl₃/CH₃OH to afford 1.05 g (97%) of pure nickel 5,15-bis-(4-carbomethoxyphenyl)-2,8,12,8-tetraethyl-3,7,13,17-tetramethylporphyrin. ¹H-NMR (300 MHZ, CDCl₃) δ 1.60 (12H, t, —CH₂CH₃), 2.21 (12H, s, —CH₃), 3.68 (8 H, q, —CH₂CH₃), 4.08 (6H, s, —CO₂CH₃), 7.96 (4H, d, Ar—H), 8.32 (4H, d, Ar—H), 9.44 (2H, s, H meso); MS m/z: 803.5 (M+H)⁺ (Calc. M=802.3); UV/vis (CH₂Cl₂) 235, 351, 406, 530, 564 nm.

A Vilsmeier reagent was prepared as follows. Twenty mL of DMF was added to a 250 mL round bottomed flask equipped with a stirring bar and a three-way adapter. The flask and its contents were cooled to 5–10° C. before and during the dropwise addition of 10 mL of POCl₃. The resulting viscous liquid was stirred at room temperature under an atmosphere of N₂ for an additional 25 minutes.

At the same time that the Vilsmeier reagent was being prepared, 1.0 g (1.37 mmole) of the nickel porphyrin was dissolved in 600 mL of 1,2-dichloroethane and cooled to 5–0° C. The Vilsmeier reagent was added dropwise to the porphyrin solution over a 10 minute period. The stirring was continued for 10 more minutes at 5° C. and then at room temperature for 2.5 hours. During this period the solution turned from a red color to green. Aqueous sodium bicarbonate with an excess of solid sodium bicarbonate was added to the reaction mixture with caution. The two-phase mixture was warmed to 40° C. and kept at this temperature for 16 hours with vigorous stirring. The green organic solution was collected and concentrated under vacuum. The residue was redissolved in diethyl ether and washed with water, dried over anhydrous sodium sulfate and then concentrated. The product was chromatographed on silica gel (CH₂Cl₂: acetone 0.5–2%) to yield 1.08 g (94% yield) of the desired nickel meso-formylporphyrin. $^1$H-NMR (300 MHZ, CDCl$_3$) δ 1.40–1.60 (12H, m, —CH$_2$CH$_3$), 1.99 (6H, s, —CH$_3$), 2.02 (6H, s, —CH$_3$), 3.40–3.60 (8H, m, —C$_2$CH$_3$), 4.06 (6H, S, —CO$_2$CH$_3$), 7.82 (4H, d, Ar—H), 8.29 (4H, d, Ar—H), 9.03 ($^1$H, s, H meso), 11.23 (1H, s, —CHO; MS m/z: 831.3 (M+H)$^+$ (Calc. M=830.3); UV/vis (CH$_2$CL$_2$) 330, 438,668 nm.

To a 250 mL round bottomed flask equipped with a condenser and a three way adapter was added 3.76 g (10.0 mmole) of N,N-diethylformamidomethyltriphenylphosphonium bromide and 100 mL of o-xylene. The mixture was stirred under N$_2$ as 0.4 g (10.0 mmole) of NaH (60% oil dispersion) was added. The stirring was continued until all the phosphonium salt reacted. At this point the nickel meso-formylporphyrin prepared above (0.416 g, 0.50 mmole) was added and the reaction mixture was warmed to reflux for 30 hours. After cooling the reaction mixture, the solvent was removed under vacuum and the residue was redissolved in dichloromethane. The solution was washed with citric acid and then with aqueous sodium bicarbonate. The solvent was evaporated and the residue was chromatographed on silica gel (CH$_2$Cl$_2$: acetone 2–4%) to give 427 mg (92% yield) of the desired nickel meso-acrylamidoporphyrin. $^1$H-NMR (300 MHZ, CDCl$_3$) δ 0.86 (3H, t, —NCH$_2$CH$_3$), 1.17 (3H, t, —NCH$_2$CH$_3$), 1.45–1.58 (12H, m, —CH$_2$CH$_3$), 2.05 (6H, s, —CH$_3$), 2.11 (6H, s, —CH$_3$), 3.10 (2H, q, —NCH$_2$CH$_3$), 3.43–3.61 (10 H, m, —CH$_2$CH$_3$ and —NCH$_2$CH$_3$), 4.06 (6H, S, —CO$_2$H$_3$), 5.56 (1H, s, vinyl-H), 7.89 (4H, br, Ar—H), 8.30 (4H, d, Ar—H), 9.17 (1H, s, H meso), 9.77 (1H, d, vinyl-H); MS m/z: 928.5 (M+H)$^+$ (Calc. M=927.4); UV/vis (CH$_2$Cl$_2$) 316, 426, 550, 586 mn.

To a 250 mL round bottomed flask equipped with a stirring bar and a three way adapter was added 0.4 g (0.43 mmole) of the nickel meso-acrylamidoporphyrin prepared as above and 70 mL of trifluoroacetic acid. The dark solution was stirred at room temperature under a N$_2$ atmosphere for 1 hour. The reaction mixture was diluted with dichloromethane and washed with water until neutral. The solvent was evaporated and the residue was chromatographed on silica gel (CHCl$_3$: methanol 3%) to give 342 mg (91%) of the desired free base meso-acrylamidoporphyrin. $^1$H-NMR (300 MHZ, CDCl$_3$) δ -2.00 (2H, s, —NH), 1.11 (3H, t, —NCH$_2$CH$_3$), 1.20–1.40 (9H, m, —CH$_2$CH$_3$ and —NCH$_2$CH$_3$), 1.57 (6H, t, —CH$_2$CH$_3$), 2.06 (6H, s, —CH$_3$), 2.23 (6H, s, —CH$_3$), 3.30–3.80 (12H, m, —CH$_2$CH$_3$ and —NCH$_2$CH$_3$), 4.11 (6H, s, —CO$_2$CH$_3$), 6.41 (1H, d, vinyl-H), 8.19 (4H, d, Ar—), 8.43 (4H, d, Ar—H), 9.63 (1H, s, H meso), 10.24 (1H, d, vinyl-H); MS m/z: 872.1 (M+H)$^+$ (Calc. M=871.5); UV/vis (CH$_2$Cl$_2$) 236, 340, 438, 530, 602 nm.

The purpurin was prepared from the free base meso-acrylamidoporphyrin following an accordance with Gunter et al., Australian J. Chem., 1990, 43, 1839–1860. To a 100 mL round bottomed flask equipped with a stirring bar and a three way adapter was added 0.2 g (0.23 mmole) of the free base meso-acrylamidoporphyrin, 39 mL o-dichlorobenzene and 2.6 mL piperidine. The solution was flushed with N$_2$ and the reaction mixture was warmed to 120° C. under a N$_2$ atmosphere. After 24 hours, the reaction mixture was cooled and diluted with dichloromethane. This solution was washed with diluted HCl and then with sodium bicarbonate. The organic layer was concentrated to a dark solid and this material was chromatographed on silica gel (CH$_2$Cl$_2$: acetone 5–8%) to give 90 mg (45% yield) of the expected purpurin diester. $^1$H-NMR (300 MHZ, CDCl$_3$) δ -0.46 (1H, s, —NH), -0.26 (3H, t, —CH$_3$), 0.50 (1H, s, —NH), 1.26–1.73 (16H, m, Pur—CH$_3$, —NCH$_2$CH$_3$ and Pur 23-CH$_2$CH$_3$) 2.12 (3H, s, Pur—CH$_3$), 2.23 (3H, s, Pur—CH$_3$), 2.25 (3H, s, Pur—CH$_3$), 2.53 (Pur 23-CH$_2$CH$_3$), 3.30–3.90 (10H, m, —CH$_2$CH$_3$ and —NCH$_2$CH$_3$), 4.07 (3H, s, —CO$_2$CH$_3$), 4.10 (3H, s, —CO$_2$CH$_3$) 4.53 (1H, q, Pur 18-H), 8.44–7.37 (8H, m, Ar—H), 8.61 (1H, s, Pur 21-H), 9.58 (1H, s, Pur 11-H meso); MS m/z: 872.3 (M+H)$^+$ (Calc. M=871.5); UV/vis (CH$_2$Cl$_2$) 237, 287, 314, 432, 538, 576, 634, 690 nm.

To a 250 mL round-bottomed flask equipped with a stirring bar and a three way adapter was added 0.1 g (0.115 mmole) of purpurin diester, 100 mL of THF and 20 mL of methanol. The solution was stirred under a nitrogen atmosphere as 3 mL of 10% aqueous KOH was added. After the addition of the base the solution was warmed to 40° C. for 24 hours. Thin layer chromatography (TLC) indicated that a single polar material had formed. The reaction mixture was poured into chloroform and washed with diluted citric acid. The organic layer was further washed with water (×2) and concentrated, and the residue was dried under vacuum. The purpurin diacid was used without further purification in the following step.

To a 100 mL round-bottomed flask equipped with a stirring bar and a three way adapter was added 80 mg (0.095 mmole) of the purpurin diacid, 25 mL of benzene and 153 μL (1.90 mmole) of pyridine. The mixture was stirred under nitrogen as 69 μL (0.948 mmole) of thionyl chloride was added dropwise. The stirring was continued at room temperature for 1 hour. After that time the solvent was removed under reduced pressure. An aliquot of benzene was added and also distilled under reduced pressure. The residue was redissolved in dichloromethane (20 mL) that contained 150 μL of pyridine. To this mixture was added 7'-apo-7'-(4-aminophenyl)-β-carotene (96 mg, 0.190 mmole), as described in Gust et al., Methods in Enzymology, 1992, 213, 87–100. After stirring for 15 minutes, methanol (1 mL) was added to the reaction mixture and the stirring was continued for an additional 15 minutes. The contents of the flask were diluted with dichloromethane (100 mL) and the solution was washed with dilute citric acid and then with aqueous sodium bicarbonate. Once dried over anhydrous sodium sulfate, the solvent was removed and the residue was chromatographed on silica gel with toluene/6–10% ethyl acetate as the solvent. Further purification by column chromatography on silica gel with dichloromethane/1–3% acetone afforded 8 mg (5% yield) of the desired dicarotenopurpurin. $^1$H-NMR (500 MHz, CDCl$_3$) δ -0.18 (1H, brs, —NH), 0.28 (3H, t, 24-CH$_3$), 0.55 (1H, brs, —NH), 1.04 (12 H, s, Car 16-CH$_3$, Car 17-CH$_3$), 1.34 (6H, t, —NCH$_2$CH$_3$), 1.40–1.70 (17H, m, Car 2-CH$_2$, Car 3-CH$_2$, Pur 3-CH$_2$CH$_3$. Pur 9-CH2CH$_3$, Pur 13-CH$_2$CH$_3$), 1.72 (6H, s, Car 18-CH$_3$), 1.98–2.01 (18H, 3s, Car 19-CH$_3$, Car 20-CH$_3$, Car 20'-CH$_3$), 2.08 (6H, s, Car 19'-CH$_3$), 2.10 (3H, s, Pur—CH$_3$), 2.20 (1H, m, Pur 19-CH$_2$CH$_3$), 2.22 (3H, s, Pur—CH$_3$), 2.36 (3H, s, Pur—CH$_3$), 2.65 (1H, m, Pur 19-CH$_2$CH$_3$), 3.40–400 (10H, m, Pur 3-CH$_2$CH$_3$, Pur 9-CH$_2$CH$_3$, Pur 13-CH$_2$CH$_3$, —NCH$_2$CH$_3$), 4.66 (1H, s, Pur 25 =CH—), 5.50 (1H, s, Pur 25 =CH—), 6.10–7.00 (28H, m, Car =CH—), 7.50–8.40 (16H, m, Pur Ar—H, Car Ar—H), 8.51, (1H, s, Pur 21-H), 9.59 (1H, Pur 11-H meso); MS m/z: 1819.4 (M+2)$^+$; UV/vis (CH$_2$Cl$_2$) 446, 478, 512, 584, 642, 702 nm.

These type B carotenopurpurins are designed to be administered by injection or by other means to localize preferentially in pathology or target tissue tissue, to absorb light at 700 nm or greater, especially at 710 nm, and thereupon fluoresce at a longer wavelength than the absorbance wavelength in accordance with the general description above. The use of diagnostic light having a wavelength in the 700 nm region allows for deeper penetration of the light, for imaging deeper pathology or target tissue tissues, and reduced tissue damage relative to agents absorbing only at shorter wavelength. Light absorption, fluorescence or both can be detected by either eye or instrumental methods, thus identifying and demarcating the pathology or target tissue tissue. Furthermore, these compounds are designed to quench the purpurin triplet states by triplet-triplet energy transfer to the attached carotenoid. This will prevent formation of singlet oxygen by energy transfer from the purpurin triplet states, and thus prevent damage to healthy tissue caused by singlet oxygen, or long-lived purpurin triplet states.

Example 3

Carotenoporphyrins consisting of carotenoid polyene, the auxiliary chromophore, covalently linked to a synthetic porphyrin (the agent) bearing one or several methoxygroups The required porphyrin, 5-(4-acetamidophenyl)-10,1 5,20-tris(3,5-dimethoxyphenyl)porphyrin, was prepared in accordance with Gust et al., Methods in Enzymology, 1992, 213, 87–100. UV/vis ($CH_2Cl_2$) 421, 516, 550, 591, 645 nm.

A portion of this porphyrin (1.2 g, 1.41 mmole) was dissolved in a mixture of 150 mL of THF, 150 mL of methanol and 90 mL of aqueous KOH (40%). The mixture was stirred at 65° C. for 24 hours under an atmosphere of $N_2$. The crude reaction was diluted with 200 mL of dichloromethane and washed with water until neutral. Chromatography on silica gel with dichloromethane and increasing amounts of acetone (0.1% to 1.5%) afforded 794 mg (70% yield) of 5-(4-aminophenyl)-10,15,20-tris(3,5-dimethoxyphenyl)porphyrin. $^1$H-NMR (300 MHz, $CDCl_3$) δ −2.79 (2H, s, —NH), 3.96 (18H, s, —$OCH_3$), 6.90 (3H, t, J=2.3 Hz, 10,15,20Ar 4-H), 7.05 (2H, d, J=8.3 Hz 5Ar 3,5-H), 7.40 (6H, d, J=2.3 Hz, 10,15,20Ar 2,6-H), 7.98(2H, d, J=8.3 Hz, 5Ar 2,6-H), 8.92 (8H, s, meso); MS m/z: 810.2 $(M+H)^+$ (Calc. M=809.3).

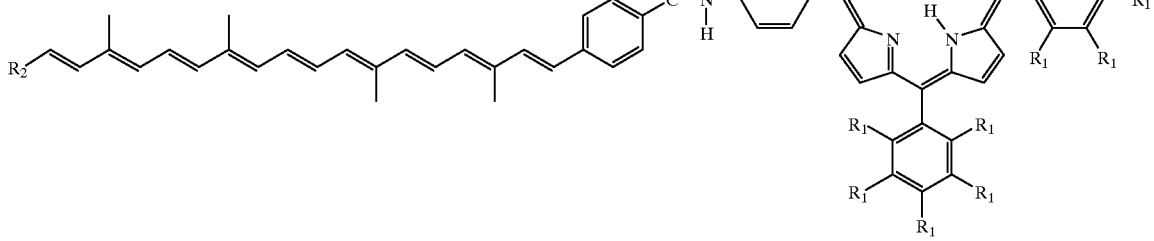

wherein $R_1$=hydrogen or substituted or unsubstituted alkyl or alkoxy group; each $R_1$ may be the same or different, wherein at least one $R_1$ is an alkoxy group;

$R_2$=hydrogen, substituted or unsubstituted alkyl or aryl group. as exemplified by The carotenoid acid chloride was prepared from 7'-apo-7'-(4-carboxyphenyl)-β-carotene in accordance with Gust et al., Methods in Enzymology, 1992, 213, 87–100. A portion of 7'-apo-7'-(4-carboxyphenyl)-p-carotene (590 mg, 1.11 mmole) was dissolved in 130 mL of dry toluene and 30 mL of dry pyridine. This solution was stirred under an atmosphere of $N_2$ while 240 μL of thionyl chloride was added.

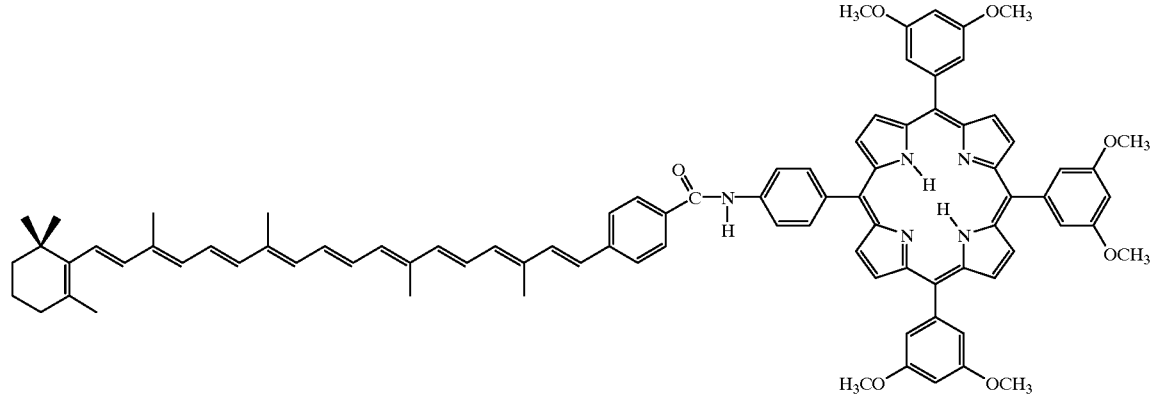

have been prepared as follows:

The mixture was kept well stirred for 30 minutes at room temperature. The solvent and excess thionyl chloride were distilled under vacuum and the residue was kept under high vacuum for approximately 30 minutes. During this time, 384 mg (0.475 mmole) of the aminoporphyrin prepared above was dissolved in 130 mL of dry toluene and 30 mL of dry pyridine. The carotenoid acid chloride was dissolved in 10 mL of toluene and 1 mL of pyridine. This solution was added to the porphyrin solution and the mixture was stirred under an atmosphere of $N_2$ for 24 hours at room temperature. The crude reaction mixture was diluted with dichloromethane and extracted with a saturated solution of sodium bicarbonate. Column chromatography on silica gel with dichloromethane and increasing amounts of ethyl acetate (0.1% to 2%) gave 490 mg of pure material as shown in FIG. 3 (78% yield). $^1$H-NMR (300 MHz, CDCl$_3$) δ −2.80 (2H, s, —NH), 1.04 (6H, s, Car 16-CH$_3$,Car 17-CH$_3$), 1.44–1.52 (2H, m, Car 2-CH$_2$), 1.57–1.68 (2H, m, Car 3-CH$_2$), 1.72 (3H, s, Car 18-CH$_3$), 1.99 (3H, s, Car 19-CH$_3$), 2.00 (3H, s, Car 20-CH$_3$), 2.01 (3H, s, Car 20'-CH$_3$), 2.02–2.04 (2H, m, Car 4-CH$_2$), 2.09 (3H, s, Car 19'-CH$_3$), 3.96 (18H, s, —OCH$_3$), 6.10–6.80 (13H, m, Car =CH—), 6.90 (3 H, t, J=2.1 Hz, 10,15,20Ar 4-H), 7.06 (1H, d, J=16 Hz, Car 8'-H), 7.41 (6H, d, J=2.1 Hz, 10,15,20Ar 2,6-H), 7.62 (2H, d, J=8 Hz, Car 1',5'-H), 7.98 (2H, J=8 Hz, Car 2',4'-H), 8.04 (2H, d, J=8.4 Hz, 5Ar 3,5-H), 8.16 (1H, s, —NH), 8.21 (2H, d, J=8.4 Hz, 5Ar 2,6-H), 8.91 (8H, m, meso); MS m/z: 1325.4 (M)$^+$ (Calc. M=1325.7); UV/vis (CH$_2$Cl$_2$) 422, 481, 513, 589, 646 nm.

These polymethoxycarotenoporphyrins are designed to be administered by injection or other means, to localize preferentially in pathology or target tissue tissue, to absorb light, especially in the 650 nm region, and thereupon fluoresce at a longer wavelength than the absorbance wavelength in accordance with the general description above. Light absorption, fluorescence or both can be detected by either eye or instrumental methods, thus identifying and demarcating the pathology or target tissue tissue. Furthermore, these compounds are designed to quench the porphyrin triplet states by triplet-triplet energy transfer to the attached carotenoid. This will prevent formation of singlet oxygen by energy transfer from the porphyrin triplet states, and thus prevent damage to healthy tissue caused by singlet oxygen, or long-lived porphyrin triplet states. These molecules are also designed to be readily excreted by normal tissue, including the liver and spleen.

Example 4

(Octa-alkyl carotenoporphyrins)

Carotenoporphyrins consisting of a carotenoid polyene (the auxiliary chromophore) covalently linked to a synthetic octa-alkyl porphyrin (the agent)

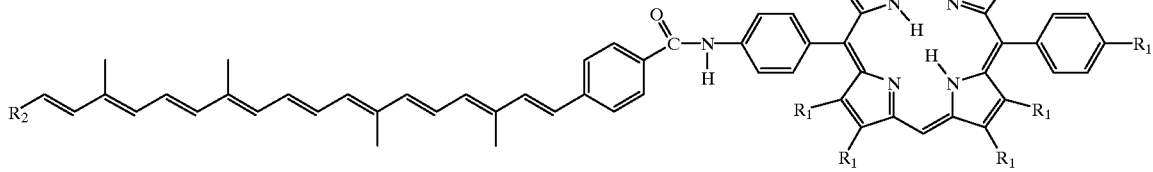

wherein
R$_1$=hydrogen, substituted or unsubstituted alkyl, alkoxy or aryl group; each R$_1$ may be the same or different,
R$_2$=hydrogen, substituted or unsubstituted alkyl or aryl group; as exemplified by sphere of N$_2$ while 240 μL of thionyl chloride was added.

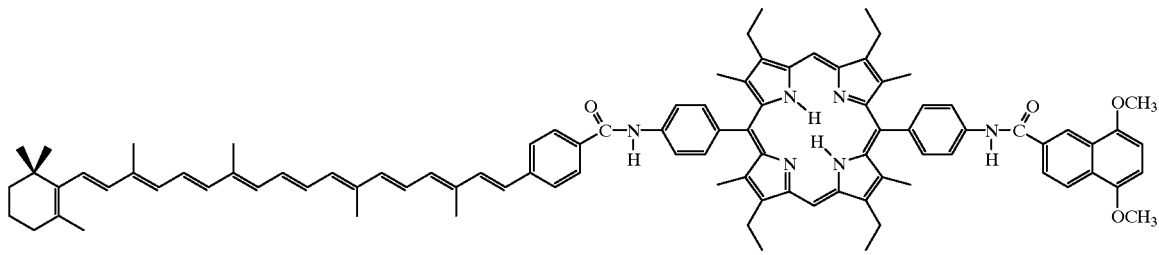

have been synthesized as follows:

To a 50-mL flask under a nitrogen atmosphere were added 46 mg (0.086 mmole) of 7'-apo-7'-(4-carboxyphenyl)-β-carotene, 12 mL of dichloromethane, 10 μL (0.091 mmole) of N-methylmorpholine, and 16 mg (0.091 mmole) of 2-chloro-4,6-dimethoxyl,3,5-triazine. The mixture was stirred for 2 hours, and 50 mg (0.057 mmole) of the required amino porphyrin prepared in accordance with Kuciauskas et al., J. Phys. Chem. B., 1997, 101, pp. 429–440. was added, along with 10 μL (0.091 mmole) of N-methylmorpholine and 11 mg (0.091 mmole) of 4-N,N-dimethylaminopyridine. After stirring for 17 hours, aqueous sodium bicarbonate was added, and the mixture stirred for 1.5 hours. Dichloromethane was added, and the resulting mixture was washed with water, dilute aqueous citric acid, and dilute aqueous sodium bicarbonate. Sodium sulfate was used to dry the organic phase, and after filtering, the solvent was distilled at reduced pressure. Chromatography of the residue on silica gel (dichloromethane containing 1–2% acetone) gave crude product, which was recrystallized from dichloromethane and methanol to give 57 mg of the compound shown in FIG. 4 (71% yield). $^1$H-NMR (300 MHz, CDCl$_3$) δ −2.40 (2H, brs, —NH), 1.04 (6H, s, Car 16-CH$_3$, Car 17-CH$_3$), 1.43–1.52 (2H, m, Car 2-CH$_2$), 1.57–1.68 (2H, m, Car 3-CH$_2$), 1.73 (3H, s, Car 18-CH$_3$), 1.78 (12H, m, 2-CH$_3$, 8-CH$_3$, 12-CH$_3$, 18-CH$_3$), 1.99 (3H, s, Car 19-CH$_3$), 2.00 (3H, s, Car 20-CH$_3$), 2.01 (3H, s, Car 20'-CH$_3$), 2.01 (2H, m, Car 4-CH$_3$), 2.10 (3H, s, Car 19'-CH$_3$), 2.56 (6H, s, 13-CH$_3$, 17-CH$_3$), 2.59 (6H, s, 3-CH$_3$, 7-CH$_3$), 4.02 (3H, s, ArOCH$_3$), 4.02 (8H, m, 2-CH$_2$, 8-CH$_2$, 12-CH$_2$, 18-CH$_2$), 4.07, (3H, s, ArOCH$_3$), 6.1–6.8 (13H, m, Car =CH—), 6.84 (2H, AB, J=9 Hz, Naphthyl 2,3-H), 7.07 (1H, d, J=16 Hz, Car 8'-H), 7.62 (2H, d, J=8 Hz, Car 1',5'-H), 7.97–8.23 (12H, m. Car 2',4'-H, 5Ar2,3,5,6-H, 15Ar2,3,5,6-H, Naphthyl 7-H, —NH), 8.42 (1 H, d7 J=9 Hz, Naphthyl 8-H,), 8.44 (1H, brs, —NH), 8.90 (1H, brs, Naphthyl 5-H), 10.24 (2H, s, 10-CH, 20-CH); MS m/z 1393 (M+H)$^-$; UV/vis (CH$_2$Cl$_2$) 410, 450 (sh), 484, 512, 574, 626 nm.

These carotenoporphyrins are designed to be administered by injection or other means, to localize preferentially in pathology or target tissue tissue, and to absorb light, especially in the 630 nm region, and thereupon fluoresce at a longer wavelength than the absorbance wavelength in accordance with the general description above. Light absorption, fluorescence or both can be detected by either eye or instrumental methods, thus identifying and demarcating the pathology or target tissue tissue.

This class of carotenoporphyrins also contains an important structural difference from other carotenoporphyrins. For steric reasons, the presence of the β-pyrrolic alkyl groups flanking the meso-aromatic rings bearing the carotenoid moiety limits the π—π overlap between the fluorophore and the carotenoid. This structural change serves to isolate the chromophores, resulting in increased fluorescence. Thus, this imaging material presents a novel method for enhancing the detection of pathology or target tissue tissue.

Furthermore, these compounds are designed to quench the porphyrin triplet states by triplet-triplet energy transfer to the attached carotenoid. This will prevent formation of singlet oxygen by energy transfer from the porphyrin triplet states, and thus prevent damage to healthy tissue caused by singlet oxygen, or long-lived porphyrin triplet states. These molecules are also designed to be readily excreted by normal tissue, including the liver and spleen.

Example 5

4-Nitroquinoline-1-oxide (4-NQO) induces dyplastic lesions and squamous cell carcinoma of the rat palate. The stage of dysplasia correlates with the 4-NQO application period. The compound synthesized in Example 3 was injected in rats in which the palate was treated with 4-NQO for 0, 6, 12 or 18 weeks. The compound was administered in a liposome preparation or an emulsion at a dosage of 5.3 micromole compound/kg.

Fluorescence images and emission spectra were taken before and at several time intervals after injection. After injection, the fluorescence in the palate tumor tissue increased homogeneously and decreased very slowly. Two peaks were observed which correspond to the in vitro fluorescence emission peaks of the compound synthesized in Example 3. Thus, it is clear that the compound was incorporated into the tumor tissue and was responsible for the observed fluorescence. The maximum in fluorescence measured 10 hours post injection was the same for the animals treated with 4-NQO for 0, 6 and 12 weeks. The rats that were treated with the tumor-inducing agent for 18 weeks, when the tumor was well-developed, showed a statistically significant higher fluorescence maximum than the rats treated for 0, 6 or 12 weeks.

Example 6

Ultraviolet B (UV-B) light induces skin cancer in hairless mice. Hairless mice were exposed to UV-B light and developed visible skin tumors. The compound synthesized in Example 3 was administered to UV-B exposed mice as well as unexposed mice in a liposome preparation or as an emulsion at a dosage of 5.3 micromol/kg. Fluorescence images and emission spectra were taken before and at several times after injection. Two peaks were observed in the fluorescence spectra after injection which correspond to the in vitro fluorescence emission peaks of the compound synthesized in Example 3. After injection of the compound, the fluorescence in healthy skin increased, and the fluorescence in the tumor tissue increased much more, indicating that the compound was transported to the tissues of the tumor and preferentially localized there. After three days, localization of fluorescence in tumors was still observable. The maximum fluorescence in normal, i.e., non UV-B treated skin, occurred between 10 hours and 20 hours after injection. In UV-B treated skin with no visible macroscopic tumors, maximum fluorescence occurred between 10 and 20 hours after injection. In visible tumor tissue, the maximum fluorescence also occurred between 10 and 20 hours post injection and was at least four times more intense than the fluorescence from skin without tumors. Thus, using this method, pathology or target tissues may be readily delineated from the surrounding skin by visual observation, photography or other imaging methods.

While not wishing to be bound by any one theory, it is thought that photoprotection by these agents arises when the carotenoid auxiliary agent rapidly quenches the cyclic tetrapyrrole triplet state by a triplet-triplet energy transfer mechanism. This returns the cyclic tetrapyrrole to the normal unexcited ground electronic state and produces the carotenoid triplet state. The carotenoid triplet state is too low in energy to produce singlet oxygen, and returns harmlessly to the carotenoid ground state with liberation of heat.

Although the invention has been described herein with reference to specific embodiments, many modifications and variations therein will readily occur to those skilled in the art. Accordingly, all such variations and modifications are included within the intended scope of the invention.

The invention claimed is:

1. A method for detection of pathology or target tissue in a mammal comprising:

(a) administering to the mammal an effective amount of an imaging material comprising a compound having the formula:

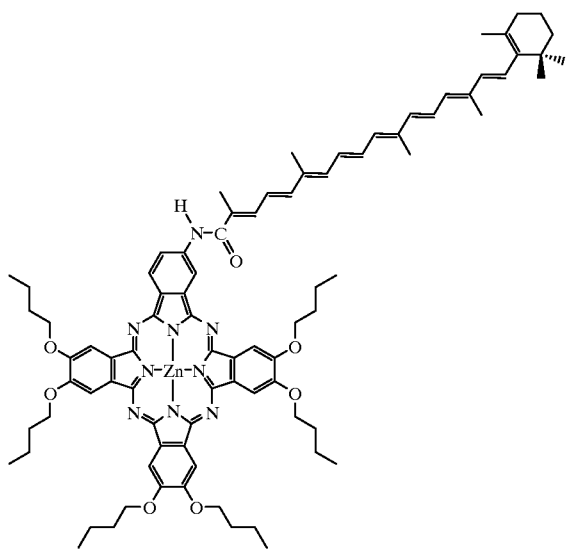

(b) allowing the imaging agent to localize in the pathology or target tissue, and
(c) exposing the mammal to electromagnetic radiation having a wavelength between about 600 nm and 1100 nm whereby the imaging material fluoresces or otherwise emits light.

2. The method of claim 1 wherein said pathology is a tumor.

3. The method of claim 1 wherein said pathology is atherosclerotic tissue.

4. The method of claim 1 wherein said pathology is arthritic tissue.

5. The method of claim 1 wherein said pathology is diseased blood vessels.

6. The method of claim 1 wherein the imaging material is administered orally, dermally, intravenously or by inhalation.

7. The method of claim 6 wherein the imaging material is administered orally, dermally, intravenously or by inhalation as a soluble emulsion.

8. The method of claim 1 wherein the imaging material is incorporated into liposomes prior to administration.

* * * * *

UNITED STATES PATENT AND TRADEMARK OFFICE
CERTIFICATE OF CORRECTION

PATENT NO. : 6,183,727 B1
DATED : February 6, 2001
INVENTOR(S) : Gust, Jr. et al.

It is certified that error appears in the above-identified patent and that said Letters Patent is hereby corrected as shown below:

Column 10,
Line 29, "MHZ" should read -- MHz --

Column 12,
Line 43, "1,2-dibromo4,5-" should read -- 1,2-dibromo-4,5- --

Column 13,
Line 15, "MHZ" should read -- MHz --

Column 14,
Line 7, "MHZ" should read -- MHz --
Line 16, "1H" should read -- 11H --
Line 20, "0H" (zero-H) should read -- OH --
Lines 26, 34 and 38, delete "tissue" (second occurence)

Column 15,
Line 49, "$^1$H-NM" should read -- $^1$H-NMR --; and "MHZ" should read -- MHz --.

Column 16,
Line 20, "MHZ" should read -- MHz --

Column 17,
Line 1, "MHZ" should read -- MHz --
Line 3, "—C$_2$CH$_3$" should read -- —CH$_2$CH$_3$ --
Line 6, "CH$_2$CL$_2$" should read -- CH$_2$Cl$_2$ --
Line 24, "MHZ" should read -- MHz --
Line 29, "—CO$_2$H$_3$" should read -- —CO$_2$CH$_3$ --
Line 32, "nm." should read -- nm. --
Line 43, "MHZ" should read -- MHz --
Line 48, "Ar—" should read -- Ar—H --
Line 66, "MHZ" should read -- MHz --

Column 18,
Line 50, "CH2CH$_3$" should read -- CH$_2$CH$_3$ --
Line 65, delete "tissue" (second occurence)

UNITED STATES PATENT AND TRADEMARK OFFICE
CERTIFICATE OF CORRECTION

PATENT NO. : 6,183,727 B1
DATED : February 6, 2001
INVENTOR(S) : Gust, Jr. et al.

It is certified that error appears in the above-identified patent and that said Letters Patent is hereby corrected as shown below:

Column 19,
Lines 3 and 7, delete "tissue" (second occurence)

Column 20,
Line 1, "1" should read -- 15, --
Line 2, "5," should be deleted
Line 44, "-p-" should read -- -ß- --

Column 21,
Line 25, "SAr" should read -- 5Ar --

Column 22,
Lines 3 and 9, delete "tissue" (second occurence)

Column 23,
Line 33, "m." should read -- m, --
Lines 40, 46 and 55, delete "tissue" (second occurence)

Signed and Sealed this

Seventh Day of May, 2002

Attest:

Attesting Officer

JAMES E. ROGAN
Director of the United States Patent and Trademark Office